United States Patent
Moe et al.

(10) Patent No.: US 8,373,568 B2
(45) Date of Patent: Feb. 12, 2013

(54) DETECTOR SYSTEM AND METHOD TO DETECT OR DETERMINE A SPECIFIC GAS WITHIN A GAS MIXTURE

(75) Inventors: Sigurd T. Moe, Oslo (NO); Niels Peter Ostbo, Oslo (NO); Knut Sandven, Snaroya (NO); Hakon Sagberg, Oslo (NO)

(73) Assignee: Gassecure AS, Oslo (NO)

( * ) Notice: Subject to any disclaimer, the term of this patent is extended or adjusted under 35 U.S.C. 154(b) by 480 days.

(21) Appl. No.: 12/668,479

(22) PCT Filed: Jul. 16, 2008

(86) PCT No.: PCT/NO2008/000267
§ 371 (c)(1),
(2), (4) Date: May 12, 2010

(87) PCT Pub. No.: WO2009/011593
PCT Pub. Date: Jan. 22, 2009

(65) Prior Publication Data
US 2010/0219960 A1    Sep. 2, 2010

(30) Foreign Application Priority Data
Jul. 17, 2007    (NO) .................................. 20073690

(51) Int. Cl.
*G08B 17/10*    (2006.01)
*G01N 7/00*    (2006.01)
(52) U.S. Cl. .......................... 340/632; 73/23.2; 73/23.31
(58) Field of Classification Search .................. 340/632; 73/23.2, 23.31
See application file for complete search history.

(56) References Cited

U.S. PATENT DOCUMENTS

| 6,321,588 | B1 | 11/2001 | Bowers et al. |
| 7,741,625 | B2 | 6/2010 | Rogne et al. |
| 7,989,821 | B2 | 8/2011 | Rogne et al. |
| 2004/0065140 | A1 | 4/2004 | Bristol |
| 2006/0114113 | A1 | 6/2006 | Yokosawa et al. |

FOREIGN PATENT DOCUMENTS

| EP | 1316799 A2 | 6/2003 |
| GB | 2364807 A | 2/2002 |
| JP | 2002109656 A | 4/2002 |
| NO | 321281 B1 | 4/2006 |
| NO | 323259 B1 | 2/2007 |
| RU | 2149381 C1 | 5/2000 |
| SU | 515062 A1 | 5/1976 |
| WO | 0016091 | 3/2000 |

OTHER PUBLICATIONS

Decision on Grant of a Patent for Invention for Russian Application No. 2010105236 (6 p.).
PCT/NO2008/000267 International Search Report, Oct. 21, 2008.

*Primary Examiner* — Brian Zimmerman
*Assistant Examiner* — Omeed Alizada
(74) *Attorney, Agent, or Firm* — Conley Rose, P.C.

(57) ABSTRACT

To achieve gas detection in a precise and reliable way, but at the same time without consuming too much energy, a gas detection system is provided which generally comprises a pair of two different gas detectors. The first detector ($D_{LP}$) is active continuously and sense substantially for an unspecific change in the local gas mixture. As a reaction upon the change, the second detector ($D_{HP}$) of the pair is activated. This detector ($D_{HP}$) performs the determination of the concentration of a specific gas or several specific gasses. The second detector ($D_{HP}$) may be of a type which consumes more power, but will be active for a short period of time before returning to an inactive state where only the first detector ($D_{LP}$) is active. The first detector ($D_{LP}$) however is of a type using little power.

34 Claims, 3 Drawing Sheets

DETECTOR SYSTEM AND METHOD TO DETECT OR DETERMINE A SPECIFIC GAS WITHIN A GAS MIXTURE

CROSS-REFERENCE TO RELATED APPLICATIONS

This application is a 35 U.S.C. §371 national stage application of PCT Application No. PCT/NO2008/000267, filed 16 Jul. 2008, and entitled Detector System and Method to Detect or Determine a Specific Gas Within a Gas Mixture, hereby incorporated herein by reference, which claims priority to Norwegian Patent Application No. 2007 3690, filed 17 Jul. 2007, hereby incorporated herein by reference.

STATEMENT REGARDING FEDERALLY-SPONSORED RESEARCH OR DEVELOPMENT

Not applicable.

TECHNICAL FIELD

The present invention relates to the field of gas detection. Specifically, the invention relates to gas detectors with low energy consumption, especially for application in areas which are dangerous with respect of gas explosions.

BACKGROUND AND PRIOR ART

Specifically on oil productions platforms and in industrial plants where hydrocarbon is handled and processed, it is important to be able as soon as possible to detect the existence of combustible gases which are leaking. In fact, more than fifty percent of gas leaks recurring on oil platforms are today detected manually. Such detection is of an incidental type and shows that there is a need for installation of more gas detectors. Gas detectors to be used on oil platforms have to fulfill stringent technical requirements. They have to be extremely reliable, sensible, EX approved and must be able to exist in harsh weather conditions over time. High technology equipment exist which can fulfill the requirements, but for extremely high price per detector and with considerable installation costs, among others because they have to be linked with fixed wiring to a central. This limits coverage of an area. Cheaper gas detector types are desirable.

It is thus an advantage that the detector arrangement is of wireless type, specifically because of the installation costs. Then it is at a same time of interest to use separate power supply for each detector arrangement, e.g. a battery supply. But it is at the same time necessary that the detector is "ON" continuously and conventional gas detectors typically draw so much current that battery operation becomes impractical or impossible.

Specifically advantageous are gas detectors of the type which are able to perform a precise determination of the concentration of a specific gas type, e.g. detector for methane have a considerable higher energy consumption than a more "unspecific" detector which can detect changes in a gas mixture, but can not determine for sure which gas has been added to the mixture.

(Examples for unspecific detector types are acoustical sensors with electrostatic, electromagnetic or piezo-electrical activation. Examples for specific detector types are photo acoustical sensors and other infrared sensors which can be made specific for e.g. methane, $C_3H_8$, $CO_2$, natural gas).

Other areas of interest with respect to disposal of the gas detector are limited areas within a manhole or tanks on vessels and down in mines lacking electricity and data communication and where one can not have fixed detector installations.

There is thus a need for a detector which both are really energy efficient and which gives good measurements of the specific gases which are considered to be dangerous in a given area.

An example of prior art is disclosed in the Patent Application EP 1 316 799 A2, where a gas detector for a specific gas is used to control a ventilation system. This publication relates mostly to algorithm for calculation of threshold values for activation.

The International Patent Application WO 00/16091 A1 describes a gas sensor group for a number of specific gases where control devices for the single gas sensors are powered down and up by a multiplexer to avoid crosstalk of signals from single sensors.

The Patent Applications US-2004065140 A1, GB-2364807 A, JP-2002109656 A and U.S. Pat. No. 6,321,588 B1 show systems and methods used to monitor changes in gas concentrations or gas leaks at hardly accessible places in industrial plants. These comprise at least one sensor and energy saving methods by sensors and other components being able to be powered down or the use of pulsed batteries.

These examples of prior art in the field do not solve the problem which is described above. The present invention seeks to satisfy the above mentioned need for reasonably priced and energy efficient gas detectors.

SUMMARY OF THE EMBODIMENTS OF THE INVENTION

To solve the above mentioned problems and to satisfy the above mentioned need, in accordance with the present invention it is provided embodiments of a detector system to detect or determine at least one specific gas in a gas mixture, where the specialty of the detector system is that it comprises
  at least one first detector which continuously monitors the gas mixture to detect a change in the composition of the mixture, and
  at least one second detector with the ability to determine the concentration of the at least one specific gas in the gas mixture wherein the second detector is arranged to be activated when the first detector detects the change.

Favorable and preferred embodiments of the detector system according to the invention appear from the attached patent claims.

The embodiments of the present invention comprise also a further aspect. The second aspect is carried out by a method to detect or determine at least one specific gas in a gas mixture, and the special features of the method is that it comprises the following:
  the gas mixture is monitored continuously with at least one first detector to detect a change in the composition of the mixture,
  at least one second detector is activated when the first detector detects the change and
  the second detector performs the determination of the concentration of the at least specific gas in the gas mixture.

Favorable and preferred embodiments of the method according to the invention will appear from the attached patent claims.

BRIEF DESCRIPTION OF THE DRAWINGS

Embodiments of the invention will be described below, and a reference to the attached drawings is given where.

DETAILED DESCRIPTION OF PREFERRED EMBODIMENTS

Figure 1:
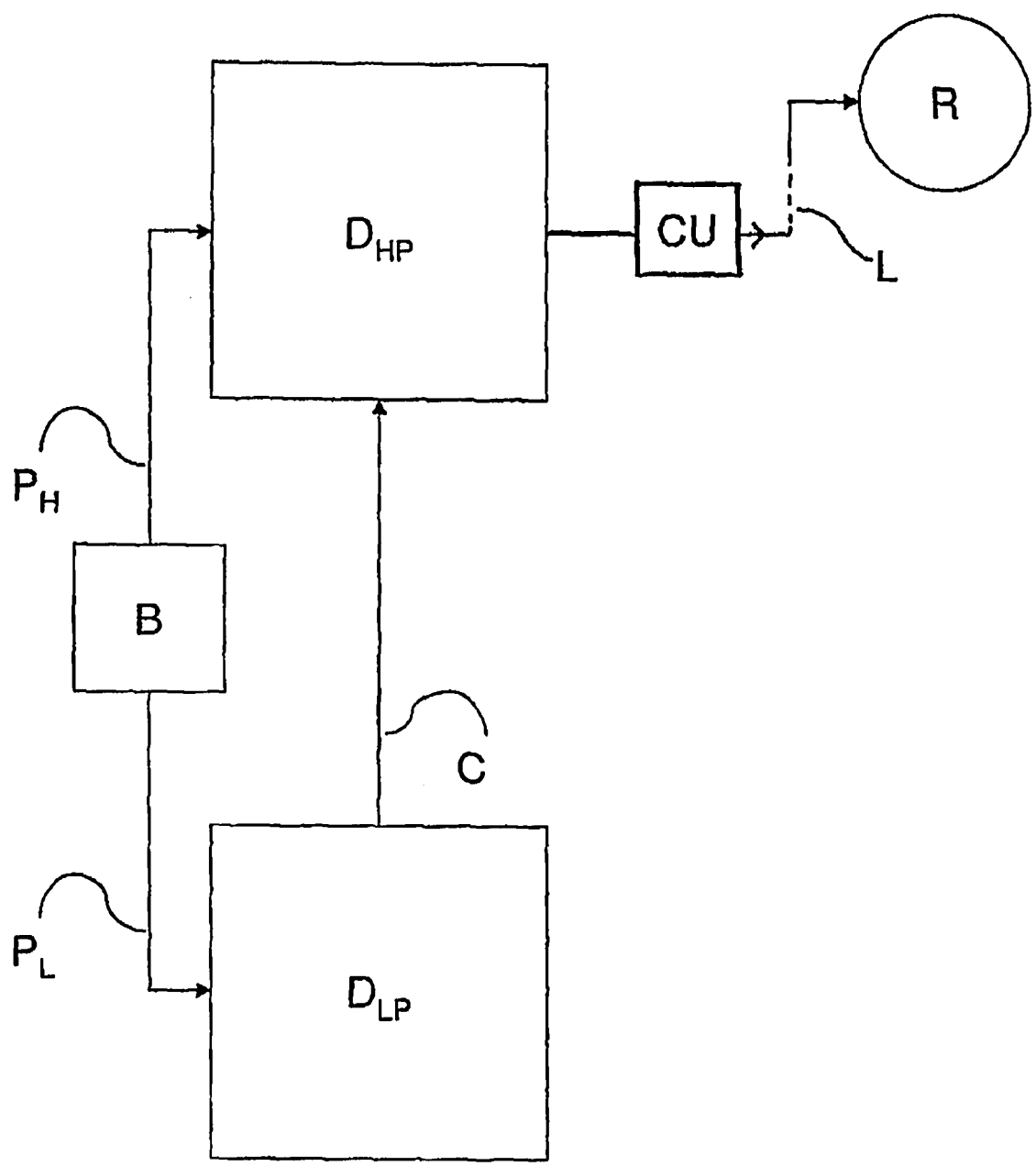
FIG. 1 shows a block diagram for a principle embodiment of the detector system according to the invention.

FIG. 1 shows a schematic diagram of a first embodiment of the invention. The main blocks are a first gas detector $D_{LP}$ with necessary equipment as electronic and sensor, and disposed close to $D_{LP}$ a second gas detector $D_{HP}$ with corresponding necessary equipment. $D_{LP}$ requires little power supply $P_L$ from the energy supply B, while $D_{HP}$ in active state requires more energy supply $P_H$ from the power supply B. The sensor in the first detector $D_{LP}$ is able to detect changes in the gas composition in the ambient atmosphere (which is not limited to the natural atmosphere, but may be any present gas mixture in the environment the detector is monitoring), but is not necessarily able to distinguish different specific gases. It does not even need to be very reliable in the sense that it may give wrong detections. The other gas detector $D_{HP}$ is arranged to measure the concentration of a specific gas, or some specific gases which are considered to be important to control in the actual environment, and it is thus activated by the first detector $D_{HP}$ only when the latter detects changes in the atmosphere composition. The "specific" detector or sensor $D_{HP}$ is of a type which uses larger amount of energy $P_H$ than the first detector $D_{LP}$, but is inactive most of the time. If this second detector $D_{HP}$ confirms the detection of the first detector $D_{LP}$ (i.e. finds a sufficient high concentration of the actual dangerous gas) it sends a message over a signal link L to a receiver R. In a special embodiment, the communication of the result of the analysis to the receiver R is performed using a radio link according to the Zigbee standard.

An embodiment of the invention is a control unit CU linked to the other detector $D_{HP}$ as shown in FIG. 1. The control unit is arranged to assess the outgoing signal from the detector $D_{HP}$ which represents a measured concentration level for the actual specific gas (or several outgoing signals for specific gases). The control unit CU is made up advantageously by a micro processor. It can be a separate unit with signal link via a wire, it can be co-located with the gas measuring unit $D_{HP}$ or it can use a radio link. In such a case the "specific" detector/measuring unit $D_{HP}$ must be equipped with a radio transmitter. This further increases the current draw of the detector, but can be acceptable because, as mentioned above, we are talking about short time activity periods for the detector $D_{HP}$.

Thus, in such a case as mentioned above, the control unit CU may be co-located with the receiver R, i.e. the receiver R can thus be looked upon to be a part of the control unit CU (i.e. to the contrary of what is shown in FIG. 1).

One function of the control unit CU can be to deactivate the second detector $D_{HP}$ right after a measurement showing a non-dangerous concentration level for the one or the several specific gases by sending the activation signal back to $D_{HP}$. (In an alternative embodiment without control unit, $D_{HP}$ can have an integrated timer which deactivates automatically on time out).

Another function of the control unit CU is to emit a signal to the outside when the measured concentration level is within a dangerous range, i.e. the signal to an remote receiver unit R as shown in FIG. 1. The signal is transmitted over a communication device L which can be a radio link, preferably of a short range type with low emitted effect, or an optical link through the atmosphere or through fibre. Then there must be disposed necessary transmitter and receiver equipment of generally known type, a control unit CU and receiver unit R. (In an alternative embodiment without control unit, the $D_{HP}$ itself may have integrated miniature transmitter which transfers signal which represents the measured value to receiver R).

Anyway such a control unit CU has stored certain threshold values for concentration in the atmosphere for the actual specific gases and the control unit will test the measured values against the threshold value to decide whether a deactivating of $D_{HP}$ shall be done, or whether a signal shall be issued to the receiver R. (NB: In order to not consuming more power than necessary in the case with a signal transfer from the control unit CU to the receiver unit $R_1$ it is possible to deactivate the second detector $D_{HP}$ again, e.g. if the measuring value does not show a further fast increase. It would be possible to apply an algorithm for "reasonable deactivation" even after a measured over-concentration. A new activation can then happen after a given time).

As a further development step of the control unit CU it can contain a recording and storing unit for values for measured gas concentrations. Such a recording unit can alternatively be disposed within the receiver R.

A natural function in connection with the gas detection system in an area where personal and/or expensive equipment is located, is an immediate alarm signal which can be followed up by surveillance personal. Such alarm and warning equipment can be disposed in the receiving unit R, typically in a surveillance-central. Or it can be integrated in the control unit CU or in the second detector $D_{HP}$ itself. Such alarm devices can comprise warning lights e.g. of a flashing type, sound sources in the form of hooters or alarm horns, as well as vibration equipment for receiving units being worn by persons.

Furthermore the receiving unit R can also be linked to the equipment which immediately assures a close-down of production or process equipment in the area where the alarm giving detector system is disposed, generally independent of if there is used equipment for giving an alarm which is sensible for humans.

It was mentioned above that the control unit CU can be linked wirelessly to the second detector $D_{HP}$ to receive a signal from the detector. The radio link can also operate the other direction e.g. a relation to the deactivation function, and $D_{HP}$ thus must have an integrated radio receiver.

In an embodiment of the invention a single control unit CU serves a number of the second detectors $D_{HP}$. A function of the control unit CU is to be reprogrammable with respect to single threshold values both for specific gases which shall determine with respect to concentration, and for single units of the second detectors $D_{HP}$. If the control unit CU is disposed in a central and together with—integrated with or as a replacement for the receiver unit R,—such threshold values could be set by an operator.

As mentioned above according to the present invention, the detector system can be used for detection of gas leaks on oil platforms and in process plants for hydrocarbons, i.e. oil and gas, which is transported and processed in large quantities. In this case it is important to monitor the natural atmosphere in situ such that gas leaks to the ambient can be detected sufficiently fast. In this case we are talking about detecting hydrocarbon gases, e.g. methane, which also can give an explosion risk.

The detector system according to the invention can also be disposed in different environments and for measuring different dangerous gases, e.g. gases wherein chlorine is a component, fluoride carbon gases, hydrogen, oxygen, hydrogen sulphide, carbon monoxide and carbon dioxide. In addition helium, water vapour and SF6-gas is of interest.

An issue with the present invention is as mentioned above, to achieve a continuous but energy saving detection, and this is achieved by the principle that a non specific gas detector consuming little energy is working continuously and wakes up a specific detector whenever a change is detected, and the specific detector then measures the concentration of the specific gas before it is deactivated again. Thus, the specific detector which consumes more energy is only active in short periods. This means that the system can work long with battery operation.

The detector $D_{LP}$ can include a sensor of a type which detects that an average and thus unspecific molecular weight for the actual gas mixture in situ is changes. This unspecific detector should be "super sensible", i.e. that it gives alert more often than really necessary, but never drops an alert about a change, i.e. even minor changes will result into a wake-up of $D_{HP}$.

The first detector $D_{LP}$ can advantageously comprise a sensor of a type which uses a micro acoustical sensor principal, with electrostatic or piezo-electrical activation.

It is further also possible as an alternative, to use a first detector $D_{LP}$ which is specific in relation to a distinct gas, as long the detector is suitable for continuous battery operation, i.e. it is drawing sufficiently little power. Such a detector will be of a type with low precision with regard to the measurement and frequently give false alarms, but this does not mean too much. Example for sensor types in such a detector are for indication of methane, metal-oxide-semi-conduct-sensors and electrochemical cells.

As an example for suitable non-specific sensors with low energy consumption to be used in the detector $D_{LP}$, in a preferred embodiment a miniature gas sensor as described in the Norwegian Patent 323259, granted 2007 Feb. 19, can be used.

Regarding the other, specific detector $D_{HP}$ it comprises in a favourable embodiment of the invention a sensor which works on the basis of the ability of the specific gas to absorb infrared radiation. So called NDIR-gass sensors (Non-Dispersive IR-) and photo acoustical sensors are candidates, specifically miniaturized detectors made by semiconductor technology. Please refer in this connection to the Norwegian Patent No. 321281 (granted 2006 Apr. 18), which shows a light source specifically well suited for such detectors.

In a specific embodiment the second detector $D_{HP}$ has an integrated intelligence represented by a micro processor with the function to chose which distinct gas to be measured (among a preset set of gases), depending on a signal level or signal type from the first detector $D_{LP}$. If the first detector immediately emits a signal which indicates a substantial change in the composition, this can be interpreted as a big leak of a substantial gas component, and it can mean that distinct gas should be checked first. In case of a less intense starting signal, a different sequence could be of interest.

It is a prerequisite in this case that the single second-detector $D_{HP}$ has the ability to measure a number of specific gases. This is possible to achieve and is realized e.g. by multi sensors of the IR-type, where the actual gases are contained in one chamber per gas with a window.

Talking about several first- and second-detectors the integrated processor-intelligence can on the basis of which first-detector DHP giving the triggering signal, decide which detectors DHP to be activated and to perform the concentration measurement. The processors at the second-detectors DHP can handle such a decision by recognizing of the signal from the single first-detector DLP.

Figure 2:
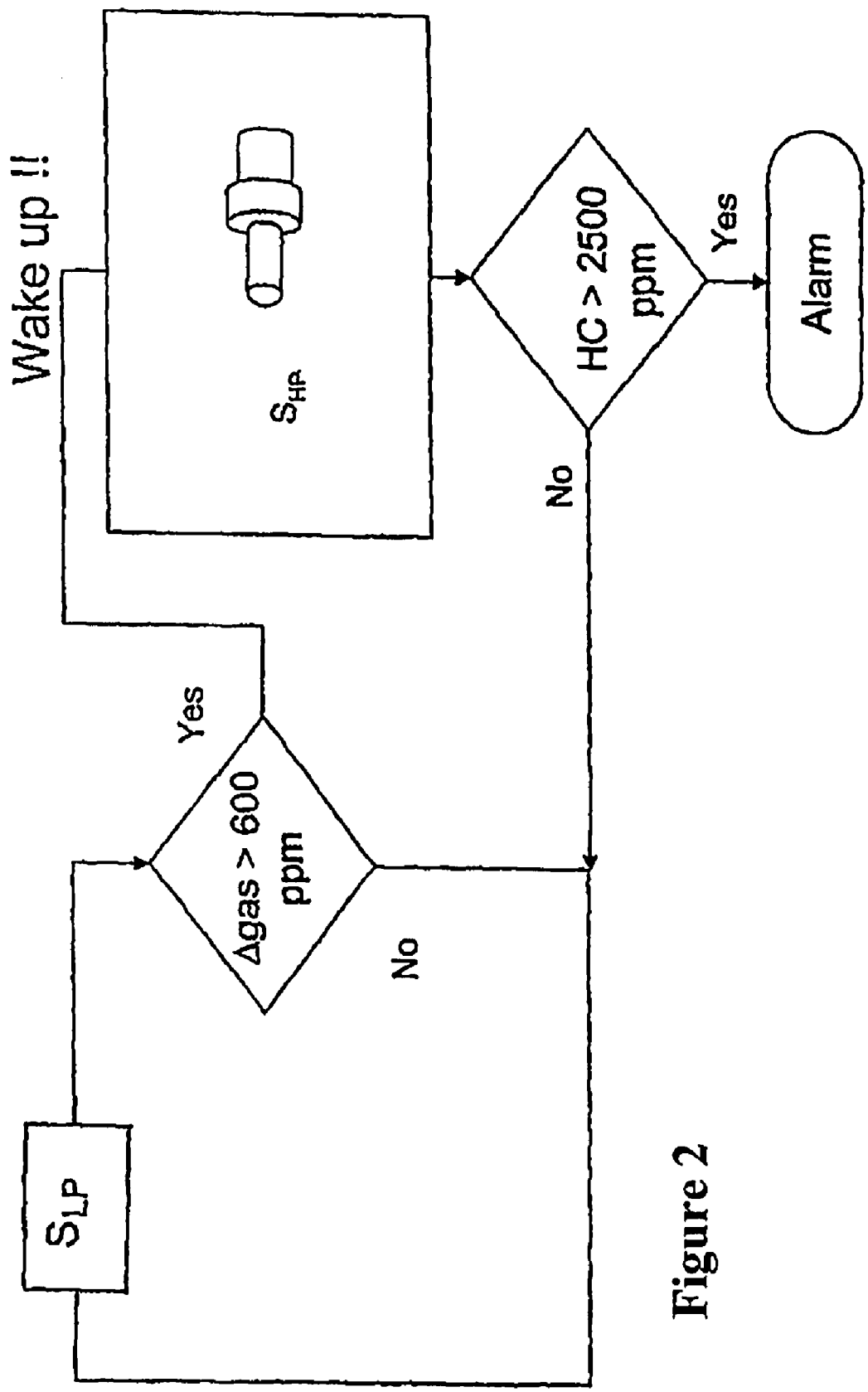
FIG. 2 shows the functional diagram about the cooperation between the detectors in the system.

FIG. 2 shows the functioning of the detector system according to the invention. A non-specific detector with the sensor $S_{LP}$ in the left part of the figure with low energy consumption, monitors in a endless loop a gas mixture—which can be the ambient atmosphere, but also a gas mixture in a pipeline or similar—and checks if the composition of the mixture stays constant or changes. (Possibly it can monitor the concentration level of a specific gas, as mentioned above). As far as the composition stays constant, the detector will continue with this monitoring without any additional action. If, however, the composition is changed in a detectable magnitude, a sensor $S_{HP}$ is activated—Wake up—in a detector in the right side of the figure which performs—with higher power consumption—a specific analysis. If the result of this analysis e.g. shows that the percentage of hydrocarbons HC in the gas mixture is lower or equal 2500 ppm, this means that the unspecific sensor $S_{LP}$ has made a fault measurement, or that the detected change in the composition of the gas mixture is related to something different than a decrease of HC, or eventually that there has been a change of HC which does not exceeds the limit for what is considered dangerous. The right detector mend the powers itself to reduce the power consumption of the total system. If, however, the estimation of the left detector is confirmed by measuring higher concentrations of hydrocarbons than e.g. 2500 ppm, an alarm is given.

Figure 3:
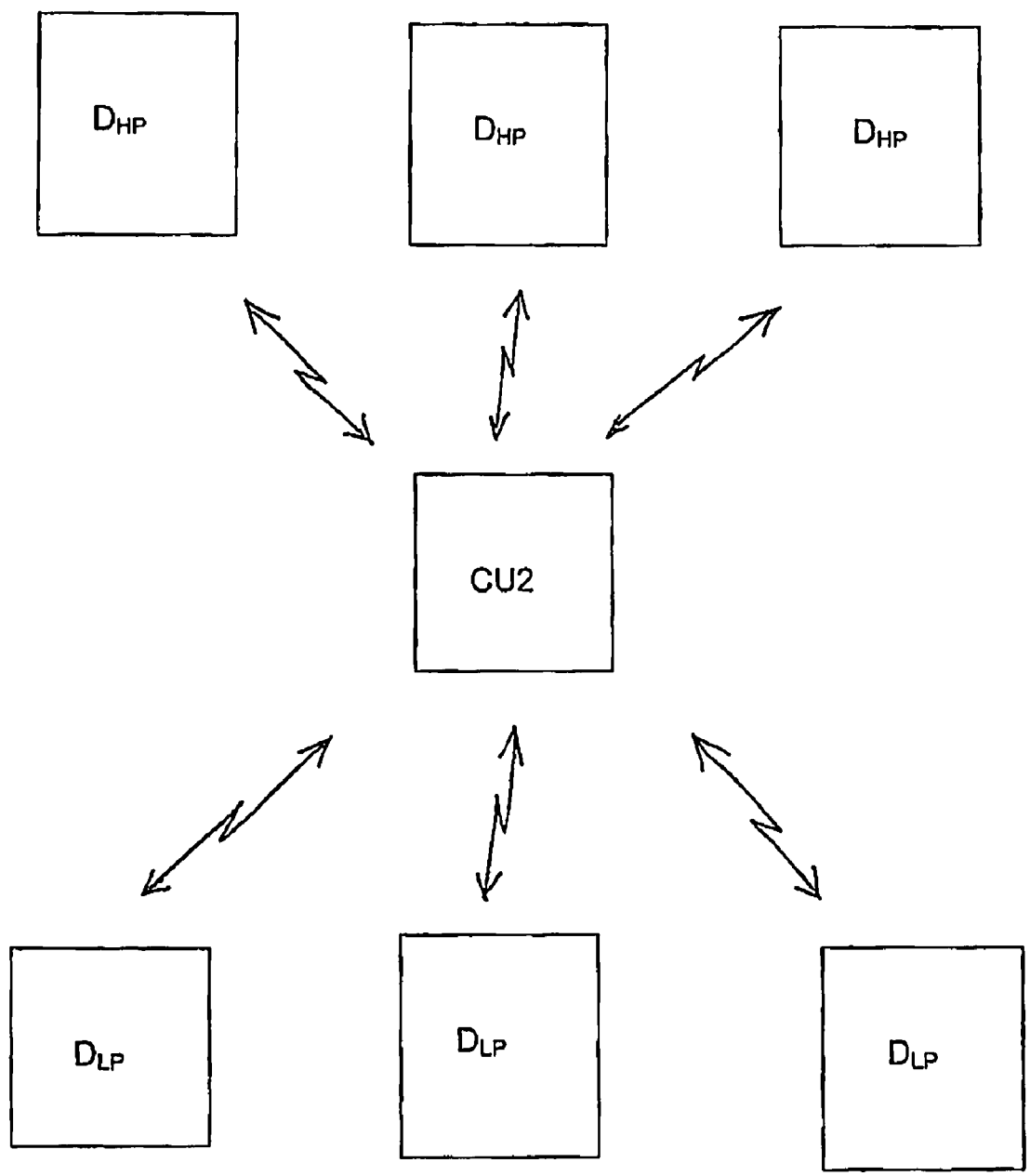
FIG. 3 shows a specific embodiment of the detector system according to the invention with a separate controller as link between groups of first and second detectors.

FIG. 3 shows another embodiment of the invention. Here a "link" between the first-detector $D_{LP}$ and the second-detector $D_{HP}$ is introduced in the form of a controller CU2. This controller CU2 which comprises a micro processor and transmitter/receiver equipment of the type which is chosen as a wireless link between the units (e.g. short range radio) may have the task to sort the incoming signals from single first-detector $D_{LP}$ to decide which specific gas shall be used to determine the concentration with all second-detectors $D_{HP}$ or with specific single ones of these. CU2, which preferably can be disposed in a central, has an overview over the placement of each single detector in the system, and can reprogrammed by the personal in accordance with the changes e.g. disposition of new detectors, changes of threshold levels and more. It is assumed that all detectors are equipped with transmitter/receiver equipment.

As can be seen in FIG. 1, in a simple embodiment of the invention with two proximate displaced detectors $D_{LP}$ and $D_{HP}$ both have power supply from a common battery B. This will be the typical form for power supply, but one would not limit one self to battery power supply. In locations with "harvestable" energy forms such as sunlight, wind or continuous vibrations, it is possible to set up an energy collecting system which supplies the detectors. One could not exclude the possibility to use known types of uninterruptible power supplies.

Above the assumption was made that the first, non-specific detector $D_{LP}$ and the second specific detector $D_{HP}$ were localized close to each other. This can in a specific embodiment mean that they are assembled together and can be delivered as a unit, even as a miniaturized type. But, in different embodiments of the detector system according to the invention where several detectors are utilized, they likely can be placed in different locations. In this case one can define an oil platform as one place even if detectors of the two different types are disposed with several tens of meters distance from each other. Such a placement can make that a CU or CU2 have a picture of how a specific gas or several specific gases are spreading.

The invention claimed is:

1. Detector system to detect or determine at least one specific gas in a gas mixture, comprising:

at least one first detector which continuously monitors said gas mixture to detect a change in said mixture composition;

at least one second detector with ability to determine a concentration of said at least one specific gas in said gas mixture; and wherein said second detector is arranged to be activated when said first detector detects said change.

2. Detector system according to claim 1, further comprising a control unit operatively linked to said second detector to evaluate a concentration measurement signal from said second detector.

3. Detector system according to claim 2, wherein said control unit is arranged to de-activate said second detector when said concentration measurement signal represents a concentration of said at least one specific gas which lies below a pre-specified value.

4. Detector system according to claim 2, wherein said control unit is arranged to emit a signal via a communication device to a receiver unit when said concentration measurement signal represents a concentration of said at least one specific gas which is higher than a pre-specified value.

5. Detector system according to claim 4, wherein at least one of said control unit and said receiver unit comprise a recording unit for measured gas concentration values.

6. Detector system according to claim 4, wherein at least one of said receiver unit, said control unit and said second detector comprise a warning or alarm device.

7. Detector system according to claim 6, wherein said warning or alarm device are capable of emitting of at least one of light, sound and vibration.

8. Detector system according to claim 4, wherein said communication device comprises at least one of an optical link and a radio link.

9. Detector system according to claim 2, wherein said control unit is linked wirelessly to said second detector.

10. Detector system according to claim 1, wherein said detectors are disposed in said natural atmosphere to monitor the natural atmosphere.

11. Detector system according to claim 1, said second detector comprising a specific ability to determine concentration of at least one of the following gasses: hydro carbons, fluoride carbons, chlorine, SF6, water vapor, helium, hydrogen, hydrogen sulphide, carbon monoxide, carbon dioxide and oxygen.

12. Detector system according to claim 1, wherein said first detector is of a type with low energy consumption, suitable for continuous battery operation.

13. Detector system according to claim 1, wherein said first detector comprising a sensor which detects changes of mean molecular weight in said gas mixture.

14. Detector system according to claim 1, wherein said first detector comprises a sensor based on a micro-acoustical principle.

15. Detector system according to claim 1, wherein said second detector comprises a sensor based on the ability of said at least one specific gas to absorb infra-red radiation, and a sensor based on a photo-acoustical principle.

16. Detector system according to claim 1, wherein said first detector includes a specific ability to detect said at least one gas, but with lower requirements for precision and with low energy consumption.

17. Detector system according to claim 1, wherein said at least one second detector comprises build-in processor-intelligence with ability to select determination of a distinct gas among said specific gasses, based on a signal level from said first detector.

18. Detector system according to claim 1, further comprising wireless signal linking between said at least one first detector and said at least second detector via a central controller with at least an ability to sort among incoming signals from single first detectors and to determine which specific gas has to be determined regarding concentration by at least one of said second detectors.

19. Detector system according to claim 1, characterized by a power supply to each of said detectors being at least one of:
an uninterruptible power supply,
a battery, and
an arrangement for energy harvesting.

20. Method to detect or to determine at least one specific gas in a gas mixture, comprising:
continuously monitoring said gas mixture with at least one first detector to detect a change in the composition of said mixture;
activating at least one second detector when said first detector detects said change; and
performing said determination of said concentration of said at least one specific gas in said gas mixture with said second detector.

21. Method according to claim 20, further comprising evaluating a concentration measurement signal from said second detector with a control unit operatively linked to said second detector.

22. Method according to claim 21, further comprising deactivating said second detector with said control unit when said concentration measurement signal represents a concentration of said at least one specific gas which lies below a pre-specified value.

23. Method according to claim 21, further comprising emitting a signal with said control unit via a communication device to a receiver unit when said concentration measurement signal represents a concentration of said at least one specific gas which is higher than a pre-specified value.

24. Method according to claim 23, further comprising recording measured gas concentration values using a recording unit using at least one of said control unit and said receiver unit.

25. Method according to claim 23, further comprising emitting an alarm using a warning or alarm device using at least one of said receiver unit, said control unit, and said second detector when the concentration of said at least one specific gas is higher than said pre-specified value.

26. Method according to claim 25, further comprising emitting a warning or alarm by use of at least one of light, sound and vibration.

27. Method according to claim 23, further comprising emitting a signal with said control unit via a communication device which comprises at least one of an optical link and a radio link.

28. Method according to claim 21, wherein said signal link between said control unit and said second detector comprises a wireless link.

29. Method according to claim 20, further comprising said first and second detectors monitoring the natural atmosphere.

30. Method according to claim 20, further comprising performing concentration determination with said second detector of at least one of the following gases: hydrocarbons, fluoride carbons, chlorine, SF6, water vapor, helium, hydrogen, hydrogen sulphide, carbon monoxide, carbon dioxide and oxygen.

31. Method according to claim 20, further comprising detecting changes in mean molecular weight in said gas mixture with a sensor in said first detector.

32. Method according to claim 20, further comprising detecting said at least one gas with said first detector specifically, but with low precision and with low energy consumption.

33. Method according to claim 20, further comprising choosing to perform determination of a distinct gas among said specific gases, with a build-in processor intelligence in said at least one second detector, on the basis of a signal level which is received from said first detector.

34. Method according to claim 20, further comprising receiving energy by each of said detectors from at least one of:
- an uninterruptible power supply;
- a battery; and
- an arrangement for harvesting of renewable energy.

* * * * *

UNITED STATES PATENT AND TRADEMARK OFFICE
CERTIFICATE OF CORRECTION

PATENT NO.        : 8,373,568 B2                                                      Page 1 of 1
APPLICATION NO.   : 12/668479
DATED             : February 12, 2013
INVENTOR(S)       : Moe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 595 days.

Signed and Sealed this
First Day of September, 2015

Michelle K. Lee
*Director of the United States Patent and Trademark Office*